(12) United States Patent
Heller

(10) Patent No.: US 9,161,699 B2
(45) Date of Patent: Oct. 20, 2015

(54) DEVICE FOR THE NON-INVASIVE DETERMINATION OF ARTERIAL BLOOD PRESSURE

(76) Inventor: Arnulf Heller, Graz (AT)

( * ) Notice: Subject to any disclaimer, the term of this patent is extended or adjusted under 35 U.S.C. 154(b) by 553 days.

(21) Appl. No.: 13/394,083

(22) PCT Filed: Sep. 2, 2010

(86) PCT No.: PCT/EP2010/062873
§ 371 (c)(1),
(2), (4) Date: May 9, 2012

(87) PCT Pub. No.: WO2011/026899
PCT Pub. Date: Mar. 10, 2011

(65) Prior Publication Data
US 2012/0220882 A1    Aug. 30, 2012

(30) Foreign Application Priority Data
Sep. 3, 2009 (AT) ................. A 1391/2009

(51) Int. Cl.
*A61B 5/02* (2006.01)
*A61B 5/021* (2006.01)
*A61B 5/053* (2006.01)

(52) U.S. Cl.
CPC ............ *A61B 5/021* (2013.01); *A61B 5/053* (2013.01)

(58) Field of Classification Search
USPC ......................................... 600/485
See application file for complete search history.

(56) References Cited

U.S. PATENT DOCUMENTS

| 4,437,469 A | 3/1984 | Djordjevich et al. |
| 4,646,754 A | 3/1987 | Seale |
| 4,807,638 A | 2/1989 | Sramek |
| 5,309,916 A | 5/1994 | Hatschek |
| 6,648,828 B2 * | 11/2003 | Friedman et al. ............ 600/506 |
| 2008/0009759 A1 | 1/2008 | Chetham |

FOREIGN PATENT DOCUMENTS

| DE | 10249863 | 5/2004 |
| WO | WO-97/37591 | 10/1997 |
| WO | WO 2007109406 A1 * | 9/2007 |
| WO | WO-2008/036011 A1 | 3/2008 |

* cited by examiner

*Primary Examiner* — Etsub Berhanu
(74) *Attorney, Agent, or Firm* — Janeen C. Vilven-Doggett; Peacock Myers, P.C.

(57) ABSTRACT

A device (10) for the non-invasive determination of arterial blood pressure of a human or animal body, comprising at least a bioimpedance measuring device (20) having a plurality of electrode pairs (21, 22, 23) for capturing the admittance signals (Y(t)) caused by an impressed alternating current on at least one first section of the body, wherein the captured admittance signals (Y(t)) correspond to a composite signal made of signal components of a pulse admittance ($Y_P(t)$), a respiration admittance ($Y_B(t)$) as well as a base admittance ($Y_0(t)$), as well as at least one device for the non-invasive measurement of the blood pressure (30), wherein a processor (40) of the device (10), which separates from the admittance measurement signals (Y(t)), which are received by the bioimpedance measuring device (20) from several electrode pairs (21, 22, 23) arranged at a distance from each other on at least one first section of the body, wherein the measurements are carried out multiple times, each time using electrode pairs arranged at different sites of the body and/or at respectively different measuring frequencies, at least the signal components of the pulse admittance ($Y_P(t)$) and which determines the arterial blood pressure ($P_C(t)$) from pressure signals ($P_P(t)$) of a second section of the body, which is preferably disposed at a distance from the first section, which signals are received from the blood pressure measuring device for determining a scaling factor (k).

3 Claims, 4 Drawing Sheets

DEVICE FOR THE NON-INVASIVE DETERMINATION OF ARTERIAL BLOOD PRESSURE

This application claims priority to and the benefit of International PCT Application Serial No. PCT/EP2010/062873, filed Sep. 2, 2010, and also claims priority to Austrian Patent Application No. A 1391/2009, filed Sep. 3, 2009, and both applications are incorporated by reference herein in their entirety.

The invention relates to a device for the non-invasive determination of the arterial blood pressure of a human or animal body, comprising at least a bioimpedance measuring device having a plurality of electrode pairs for capturing the admittance measurement signals caused by an impressed alternating current on at least one first section of the body, wherein the captured admittance measurement signals correspond to a composite signal made of signal components of a pulse admittance, a respiration admittance as well as a base admittance, as well as at least one device for the non-invasive measurement of the blood pressure.

Impedance cardiography has been successfully used for some time for the non-invasive, this is blood-less, measurement of certain hemodynamic parameters of the heart as well as the stroke volume or the heart-time-volume. These parameters play a decisive role in the monitoring of patients in intensive care.

In contrast to invasive methods, wherein there has to be established a catheter, in the impedance cardiography there is made use of fluctuations of the resistance across the thorax during a heart period. For this reason, there is supplied a small constant measuring current into the body, and the impedance change is determined by change of the voltage. From this curve, there may be determined then the above mentioned hemodynamic parameters. Impedance cardiography, in general, offers good correlation with the invasive standard methods, it has, however, due to its non-invasiveness, fewer complications. Another advantage of the impedance cardiography is developed by the beat-to-beat measurement of the stroke volume. In this way, the development of the patent may be assessed and monitored in real time.

In determining the stroke volume (SV) by means of impedance cardiography, there is used a simplified geometrical model for the illustration of an electric field of the thorax, which only strongly approximates the actual conditions.

During a heart period, the pressure in the aorta is increased. Due to the elasticity of the aorta walls, also the diameter of the aorta is increased, which is why the impedance of the thorax decreases. This connection between the change of the impedance of the thorax at each heart stroke and the central arterial pressure has not been used for the measurement of blood pressure so far.

When measuring the blood pressure, the pressure in a blood vessel is determined by means of a technical method. There is distinguished between the measurement of the arterial pressure, of the venous pressure as well as the measurement in the pulmonary artery (pulmonary arterial pressure) and in the pulmonary capillary region (pulmonary-capillary pressure). Whereas the majority of the methods require special procedures of examination and are special procedures, performed partly out of the routine practice, the measurement of the arterial pressure plays an important role in the daily routine of medicine, as it is easy to be performed.

There is made a distinction between the direct invasive pressure measurement by means of a pressure sensor in a blood vessel and the indirect non-invasive measurement, which is carried out by way of a cuff at an extremity.

In the direct and invasive measurement (frequently abbreviated with "IBP", invasive blood pressure), a vessel, for example a peripheral artery, most frequently the arteria radialis, is punctured, and a pressure sensor is introduced, by means of which the pressure course may be displayed on a monitor. The measurement is precise and offers the advantage of a continuous monitoring; in addition, the device determines the pulse frequency and the average arterial pressure when measuring the arterial pressure. As the method is invasive, which is associated with the risk of bleeding, infections and nerve injuries, it is mainly used by anaesthetists for monitoring during an operation and in intensive care units. By means of an invasive pressure measurement, it is also possible to measure the central-venous pressure (in the superior vena cava) and the pulmonary-arterial pressure (in the pulmonary artery).

In the indirect and non-invasive arterial pressure measurement, the arterial pressure is measured by means of a blood pressure measuring device at an extremity, usually at an arm. Whereas the measurement of this type is not as precise as the direct method, its simple, fast, harmless and cheap practice makes it a method of choice in the majority of the medicinal fields. There is distinguished between the manual measurement and the automated measurement by means of a digital blood pressure measuring device. It is important therefore for the cuff being positioned at the height of the heart, to which there is to be paid attention especially when using wrist devices. The manual measurement may be carried out auscultatorily, palpatorily and oscillatorily. The values of the individual methods then slightly diverge from each other.

In the auscultatory measurement, there is inflated a pressure cuff of an appropriate width at the upper arm beyond the expected arterial pressure. When slowly deflating, there may be heard the appearance and then the disappearance of a Korotkow sound using a stethoscope across the artery of the arm. The pressure, which may be read at the beginning of the emergence of the sound heard on the scale of the measuring device, corresponds to the upper systolic arterial pressure value, this is, the systolic pressure is at this point bigger than the pressure of the cuff. The pressure is then further reduced at an appropriate rate. If the cuff pressure is lower than the minimal arterial pressure value, the sound will suspend. This value is designated as diastolic pressure and noted as so-called lower value. The auscultatory measurement is the standard procedure of the non-invasive measurement methods.

Also in the palpatory measurement, there is applied a pressure cuff onto the upper arm, with the pulse being sensed at the arteria radialis when the pressure is reduced. The pressure, which may be read, when the pulse is sensed for the first time, on the scale of the measuring device, corresponds to the upper systolic arterial pressure value. The diastolic value cannot be determined in this way. The method is suitable in a loud surrounding, in particular in ambulance service.

The oscillatory measurement is carried out like the two other methods, with the upper and the lower value being estimated by way of the amplitude course of a pulse-synchronous point deflection at the measuring device, which illustrates the transfer of vibrations from the vessel wall to the pressure cuff. In the manual measurement, there may only be obtained rather imprecise results. This measuring principle is, however, reliably used by measuring machines for the continuous monitoring, for example, following a surgical procedure in the recovery room. These measure, as an alternative to the invasive arterial pressure measurement, the arterial pressure of the patient in an interval of a few minutes. The oscillatory measurement process is also used in the now rather common wrist measuring devices.

The disadvantage of this measurement method using an upper arm pressure cuff, however, is that the shortest measuring interval possible of several minutes may, in particular in the case of intensive care medicine, be too long and that this blood pressure measurement does not make available a beat-to-beat signal. In particular if a hypotonic crisis, this is a phase with a too low blood pressure, is not recognized in time, the post-operative mortality risk may be substantially increased. A non-invasive, continuous blood pressure measurement, which may recognize blood pressure drops without delay, hence, is especially desirable.

The present invention, hence, aims at preventing the disadvantages known from the state of the art for the non-invasive determination of the arterial blood pressure and, for this reason, providing a device, which is embodied according to the preamble of claim 1 with the features of the characterizing part of the claim 1.

The sub-claims relate to especially advantageous embodiments of the invention.

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the inventions and are not to be construed as limiting the invention. In the drawings.

Figure 1:
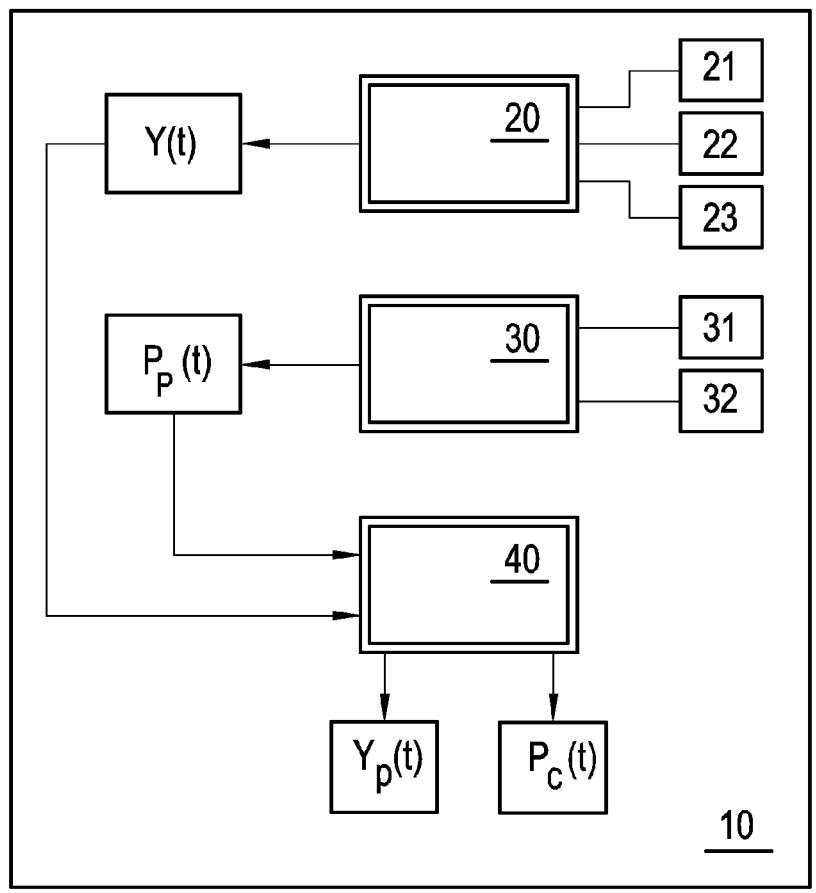
FIG. 1 is a drawing which illustrates a schematic of a device 10 according to an embodiment of the present invention having a bioimpedance measuring device and a plurality of electrode pairs for capturing the admittance signals.

A device according to the invention for the non-invasive determination of the arterial blood pressure of a human or animal body preferably comprises at least a bioimpedance measuring device having a plurality of electrode pairs for capturing the admittance measurement signals caused by an impressed alternating current on at least one first section of the body, wherein the captured admittance measurement signals correspond to a composite signal made of signal components of a pulse admittance, a respiration admittance as well as a base admittance, as well as at least one device for the non-invasive measurement of the blood pressure, wherein a processor of the device, which separates from the admittance measurement signals, which are received by the bioimpedance measurement device from several electrode pairs arranged at a distance from each other on at least one first section of the body, wherein the measurements are carried out multiple times, each time using electrode pairs arranged at different sites and/or at respectively different measurement frequencies, at least the signal components of the pulse admittance and which determines the arterial blood pressure from pressure signals of a second section of the body, which is preferably disposed at a distance from the first section, which signals are received from the blood pressure measuring device for determining a scaling factor.

According to the standard, there is used for measuring the admittance by means of an impedance cardiography method a so-called 4-wire-measuring unit, wherein there is provided at least a first pair of electrodes for introducing a small constant measuring current into the body and at least a further second pair of electrodes for sensing the change of voltage. There are, e.g., used strip-like electrodes, wherein there is impressed current in a first strip electrode and there is measured the voltage at the at least second strip electrode. A first electrode strip is adhered, for example, in a human being in the region of the neck, at least two further electrode strips are electrically connected in parallel and are then attached laterally at the thorax at about the height of the sternum.

Also an arrangement of electrodes according to Einthoven is especially suitable for measuring the admittance using the device according to the invention, as this electrode arrangement is usually used for determining an electrocardiogram (ECG) and thus is well known among medical staff Furthermore, the arrangement according to Einthoven facilitates a separate capturing of the signal components of the pulse admittance as well as the perspiration admittance.

Biological tissues have a respectively characteristic, frequency-dependent course of impedance or admittance, respectively. The impedance course of, for instance, pulmonary tissue and blood are different. This condition may be used in order to separate in a suitable arrangement of several electrode pairs or in multiple measurements at different measuring frequencies the components of the respiration admittance (in order thereto, electrodes are disposed as near to the lung as possible) from the pulse admittance (electrodes are disposed as near to the heart as possible).

In a useful embodiment of the device according to the invention, the processor determines the arterial blood pressure from the admittance measurement signals and the pressure signals according to the following scheme:

measuring of the several admittance measurement signals at different body sites and/or at different measuring frequencies;

filtering the admittance measurement signals with a high-pass filter so that the lower-frequent components of the basis admittance are separated and the filtered admittance signals are received;

setting sum equations, taking into account the proportional factors of the pulse admittance as well as the respiration admittance for the filtered admittance signals:

using a source separation algorithm in order to determine the proportional factors as well as the source signal components of the pulse admittance and the respiration admittance from the sum equations;

measuring the pressure signals as reference pressure signals;

determining a scaling factor and an offset value so that the pulse admittance coincides with the pressure signals measured as reference pressure signals;

After the end of the reference measurement, the arterial blood pressure is continuously determined using the sum of the offset value with the product of scaling factor and pulse admittance.

In particular the determination of pressure signals, for example, of an upper arm measurement as reference signals has, when used in the device according to the invention, substantial advantages over a conventional upper arm pressure measurement. A conventional upper arm pressure measurement usually takes at least 30 seconds. During this period of time, the systolic pressure value at the beginning of the measurement with high cuff pressure as well as the diastolic pressure value at the end of the measure with low cuff pressure are determined. Within this period of time, the blood pressure may, however, change physiologically significantly, which cannot be detected by means of a conventional upper arm pressure measurement.

Using the pulse admittance, however, provides, when using the device according to the invention, advantageously for a relative measure for a possible change of the blood pressure on a permanent basis, which may be integrated, e.g., in an oscillometric measurement of the pressure.

Another advantageous embodiment of the invention comprises a device, wherein the processor separates from the admittance measurement signals, which are received by the bioimpedance measuring device on at least one first section of the body, using a transmission algorithm simulating the transmission of pressure waves in the body, at least the respective signal components of the pulse admittance according to the following scheme:
- filtering the admittance measuring signals with a high-pass filter so that the lower-frequent components are separated and there is received a signal of a filtered admittance;
- filtering the pressure signals with the high-pass filter so that there is received a filtered pressure signal;
- using an adaptive filter in order to determine a transmission function from the filtered pressure signal to the filtered admittance;
- using a transmission algorithm in order to determine an extrapolated transmission function;
- using an optimization algorithm, for example, according to the method of the least error squares, in order to determine a parameter vector of the used transmission algorithm as well as the scaling factor so that the error between the filtered transmission function and the product of the scaling factor is minimized with the extrapolated transmission function in a higher-frequent measurement range;
- determining the pulse admittance using the product of the scaling factor with the extrapolated transmission function and the pressure signals;
- determining the arterial blood pressure by means of the extrapolated transmission function and the pressure signals.

By filtering the lower-frequent components, there is in particular separated the component of the base admittance, this is the component of the surrounding tissue of the body. The transmission function, which is determined using an adaptive filter as functional association with a filtered pressure signal and the filtered admittance, provides for reliable estimations only in those frequency ranges, in which there may be captured sufficiently efficiently the respective input as well as the output signal. This does not apply for the lower-frequent measurement region. For this reason, there has to be determined a further transmission function that is extrapolated onto the entire frequency range, which is then applied to the unfiltered measured pressure signals and, in this way, provides for an estimated value of the pulse admittance.

By using suitable algorithms, the determination of the arterial blood pressure is carried out in real-time as a beat-to-beat determination.

Suitably for a device according to the invention a transmission line model is valid as transmission algorithm, wherein the parameter vector comprises a flow resistance parameter, a resistance parameter of the blood mass against acceleration, an elasticity parameter of the arterial wall as well as a porosity parameter.

The transmission line model fundamentally describes the transmission of electromagnetic waves in lines. By establishment of biophysical assumptions, there may also be described by ways of this model the transmission of volume and pressure pulses in elastic vessels. The configuration of the transmission line model consists of a serial arrangement of infinitesimally small, identical sections, which are each described by parameters of the parameter vector. If the parameter vector is determined and, hence, the transmission algorithm is known in the transmission line model, the arterial blood pressure along the entire transmission line may be advantageously be determined by means of this model. If, for example, the central blood pressure and the peripheral blood pressure are measured at the finger, there may also be determined a brachial blood pressure at the upper arm.

It is further advantageous that there may be obtained an improved calibration of central, radial as well as peripheral (brachial) blood pressure signals using the transmission line model in a known transmission algorithm by means of comparison of the calculated pressure signals with the actually measured pressure signals. A physician in charge, hence, may obtain any of these pressure signals from the device according to the invention, as he/she desires.

Advantageously, in an embodiment of the device according to the invention, the non-invasive blood pressure measurement is carried out discontinuously.

The blood pressure measuring device comprises, for example, a pressure cuff for application onto a body extremity. The upper arm is usually used for this purpose.

Especially usefully, in an embodiment variant of the device the non-invasive blood pressure measurement is carried out continuously.

The blood pressure measuring device, hence, comprises, for example, a finger cuff for a continuous pressure measurement. Advantageously, there is provided also during a surgical procedure a current, continuously measured blood pressure signal; measuring the pressure at the upper arm may be omitted in the case of a measurement of the blood pressure by means of a finger cuff.

Further features of the invention become obvious from the following description of exemplary embodiments and in reference to the drawings.

FIG. 1 shows in a schematically simplified form a device 10 according to the invention having a bioimpedance measuring device 20 having a plurality of electrode pairs 21, 22, 23 for capturing the admittance signals Y(t) caused by an impressed alternating current on at least one first section of a human body that is not shown, wherein the captured admittance signals Y(t), if obtained at the thorax, correspond to a composite signal made of signal components of a pulse admittance $Y_P(t)$, a respiration admittance $Y_B(t)$ as well as a base admittance $Y_0(t)$. The device 10 further comprises a device for the non-invasive blood pressure measurement 30, provided with a finger cuff pressure measuring device 31 for capturing the peripheral pulse $P_P(t)$ at a finger as well as with a pressure measuring device 32 having an upper arm cuff for capturing the systolic or diastolic, respectively, value pairs of the peripheral pulse $P_P(t)$ at the upper arm of the human body to be examined.

A processor 40 of the device 10 separates from the admittance measurement signals $Y(t)$, which are received by the bioimpedance measuring device 20 from the several electrode pairs 21, 22, 23 arranged at a distance from each other on at least one first section of the body, at least the signal components of the pulse admittance $Y_P(t)$. Further there is determined a scaling factor (k) from pressure signals $P_P(t)$ of a second section of the body, which is preferably disposed at a distance from the first section, which signals are received from the blood pressure measuring device 30. The arterial blood pressure $P_C(t)$ is then determined on the basis of the pulse admittance $Y_P(t)$.

The device 10 according to the invention is in principle suitable for the determination of the arterial blood pressure $P_C(t)$ in a human as well as in animals. The device 10 may further also be used, by the appropriate selection of electrodes, for determining the local blood pressure, for example at a leg.

Figure 2:
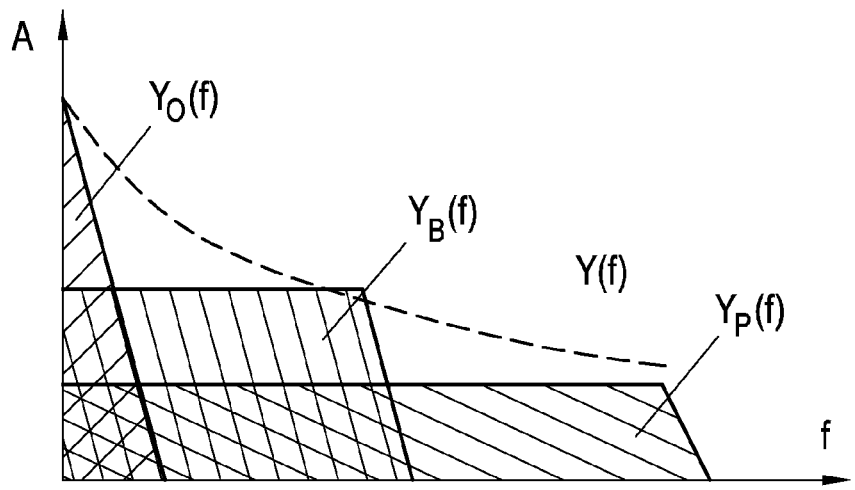
FIG. 2 is a diagram illustrating the overlapping of the signal components of the pulse admittance $Y_P(f)$, the respiration admittance $Y_B(f)$ as well as the base admittance $Y_0(f)$ into the composite signal of the measureable admittance $Y(f)$.

FIG. 2 shows in a schematic illustration in the form of a diagram the overlapping of the signal components of the pulse admittance $Y_P(f)$, the respiration admittance $Y_B(f)$ as well as the base admittance $Y_0(f)$ into the composite signal of the measureable admittance $Y(f)$—each as function of the frequency f, applied onto the abscissa of the diagram. Herein, the amplitude A is applied as ordinate value. The base admittance $Y_0(t)$—essentially conditioned by the body tissue—corresponds to a lower-frequent fundamental component at a high amplitude. This is overlapped by the respiration admittance $Y_B(t)$ up to medium frequencies as well as the pulse admittance $Y_P(t)$ up to high frequencies.

Figure 3:
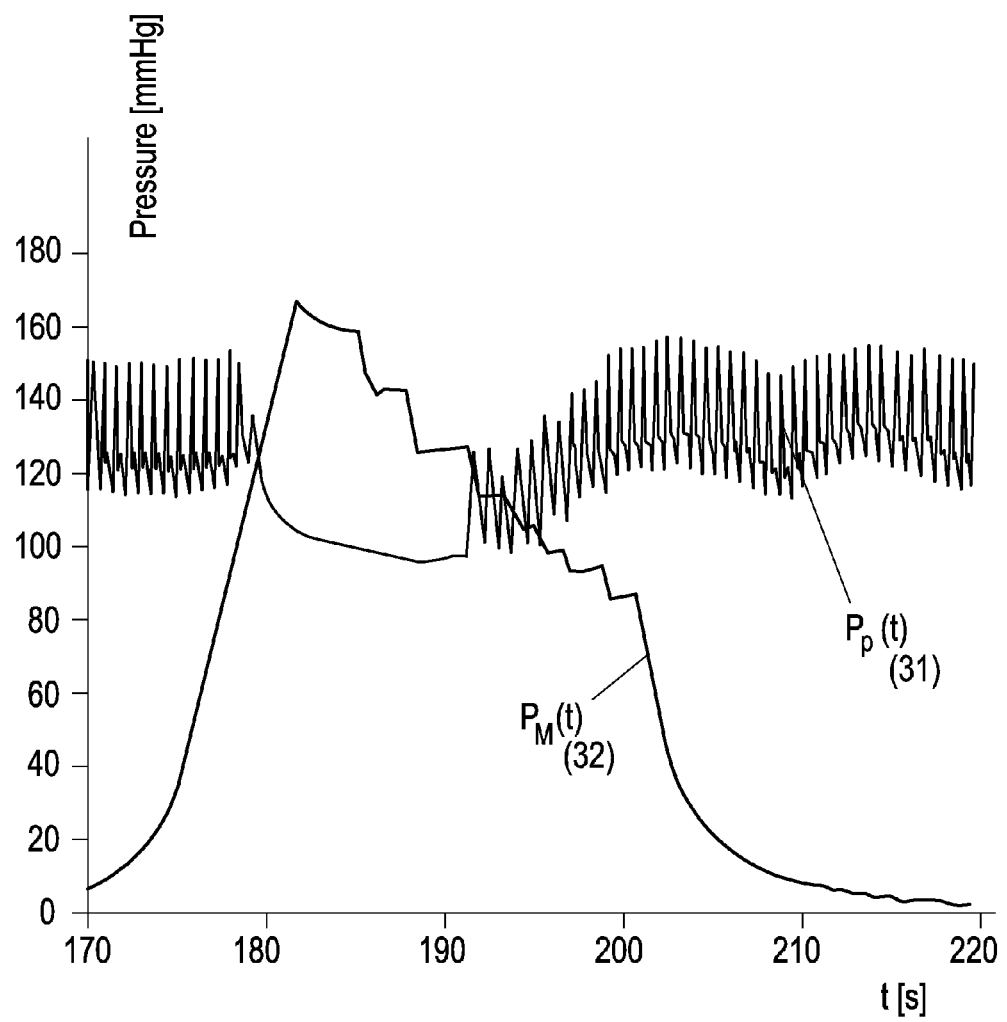
FIG. 3 is a drawing which illustrates a diagram form the two overlapped peripheral pressure signals $P_P(t)$ of a pressure measuring device having a finger cuff with the pressure signal $P_M(t)$ of a pressure measuring device having an upper arm cuff.

FIG. 3 shows in a diagram form the two overlapped peripheral pressure signals $P_P(t)$ of a pressure measuring device 31 having a finger cuff with the pressure signal $P_M(t)$ of a pressure measuring device 32 having an upper arm cuff. The pressure signals $P_P(t)$ or $P_M(t)$, respectively, are captured at the same arm. In the diagram, the measurement duration t (in seconds s) is applied to the abscissa, whereas the blood pressure (in mm Hg) is applied to the ordinate. It is surprising that the continuous signal $P_P(t)$ of the pressure measuring device 31 is falsified by the pressure measuring device 32 having an upper arm cuff during the measurement. The device according to the invention overcomes this drawback of the pressure measuring device 32 having an upper arm cuff, as the arterial blood pressure is determined by the device according to the invention without any interruption.

Figure 4:
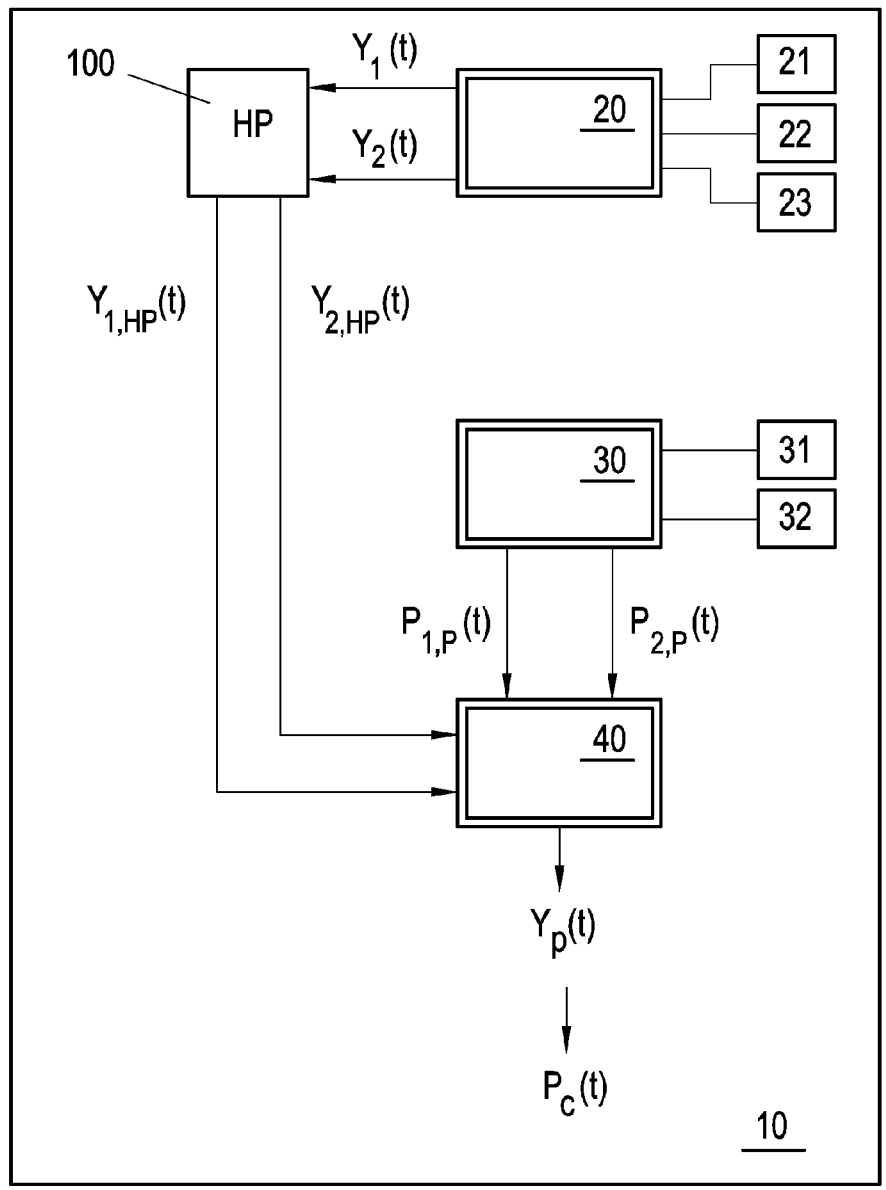
FIG. 4 is a drawing which illustrates a device according to an embodiment of the present invention having a bioimpedance measuring device having a plurality of electrode pairs for capturing the admittance measurement signals $Y_1(t)$ caused by an impressed alternating current as well as $Y_2(t)$ on at least a first section of a human body that is not displayed.

FIG. 4 shows schematically simplified a device 10 according to the invention having a bioimpedance measuring device 20 having a plurality of electrode pairs 21, 22, 23 for capturing the admittance measurement signals $Y_1(t)$ caused by an impressed alternating current as well as $Y_2(t)$ on at least a first section of a human body that is not displayed. The admittance signals $Y_1(t)$ as well as $Y_2(t)$ were received at different measurement frequencies, wherein the captured admittance measurement signals $Y(t)$, if received at the thorax, each correspond to a composite signal of signal components of a pulse admittance $Y_P(t)$, a respiration admittance $Y_B(t)$ as well as a base admittance $Y_0(t)$.

The device 10 further comprises a device for the non-invasive blood pressure measurement 30, provided with a finger cuff pressure measuring device 31 for capturing the peripheral pulse $P_P(t)$ at a finger as well as a pressure measuring device 32 having an upper arm cuff for capturing the peripheral pulse $P_P(t)$ at the upper arm of the human body to be examined. It is sufficient if the device 10 has, for example, only a pressure measuring device, this is either the pressure measuring device 31 or the pressure measuring device 32.

The several admittance measurement signals $Y_1(t)$ or $Y_2(t)$, respectively, are filtered with a high-pass filter so that the lower-frequent components of the basis admittance $Y_{1,0}(t)$ or $Y_{2,0}(t)$, respectively, are separated and so that the admittance signals $Y_{1,HP}(t)$ or $Y_{2,HP}(t)$, respectively, that are filtered by a processor 40, are received. The processor 40 sets sum equations, taking into account the proportional factors of the pulse admittance $Y_P(t)$ as well as the respiration admittance $Y_B(t)$ for the filtered admittance signals:

$$Y_{1,HP}(t) = k_{1,1} \cdot Y_B(t) + k_{1,2} \cdot Y_P(t) \quad \text{or} \quad Y_{2,HP}(t) = k_{2,1} \cdot Y_B(t) + k_{2,2} \cdot Y_P(t), \text{ respectively;}$$

Using a source separation algorithm, the processor 40 then determines the proportional factors $k_{1,1}, k_{1,2}, k_{2,1}, k_{2,2}$ as well as the source signal components of the pulse admittance $Y_P(t)$ and the respiration admittance $Y_B(t)$ from the sum equations.

Furthermore, the pressure signals $P_{1,P}(t)$ as well as $P_{2,P}(t)$ are captured by the device for the measurement of blood pressure 30 and further transmitted to the processor 40 as reference pressure signals. If there is used a pressure measuring device 32 having an upper arm cuff, the pressure signals $P_{1,P}(t)$ and $P_{2,P}(t)$, for example, correspond to an assigned value pair consisting of systolic and diastolic blood pressure. Subsequently, the processor 40 determines a scaling factor k and an offset value d so that the pulse admittance $Y_P(t)$ coincides with the pressure signals $P_{1,P}(t)$ and $P_{2,P}(t)$ measured as reference pressure signals. The relation between the individual calculation variables is, for example, as follows:

$$P_{1,P}(t) = k \cdot Y_{P,Sys} + d \text{ or } P_{2,P}(t) = k \cdot Y_{P,Dia} + d, \text{ respectively}$$

After the end of the reference measurement, the arterial blood pressure $P_C(t)$ is continuously determined by the processor 40 of the device 10 continuously using the scaling factor k and the offset value d according to the equation $P_C(t) = k \cdot Y_P(t) + d$.

Figure 5:
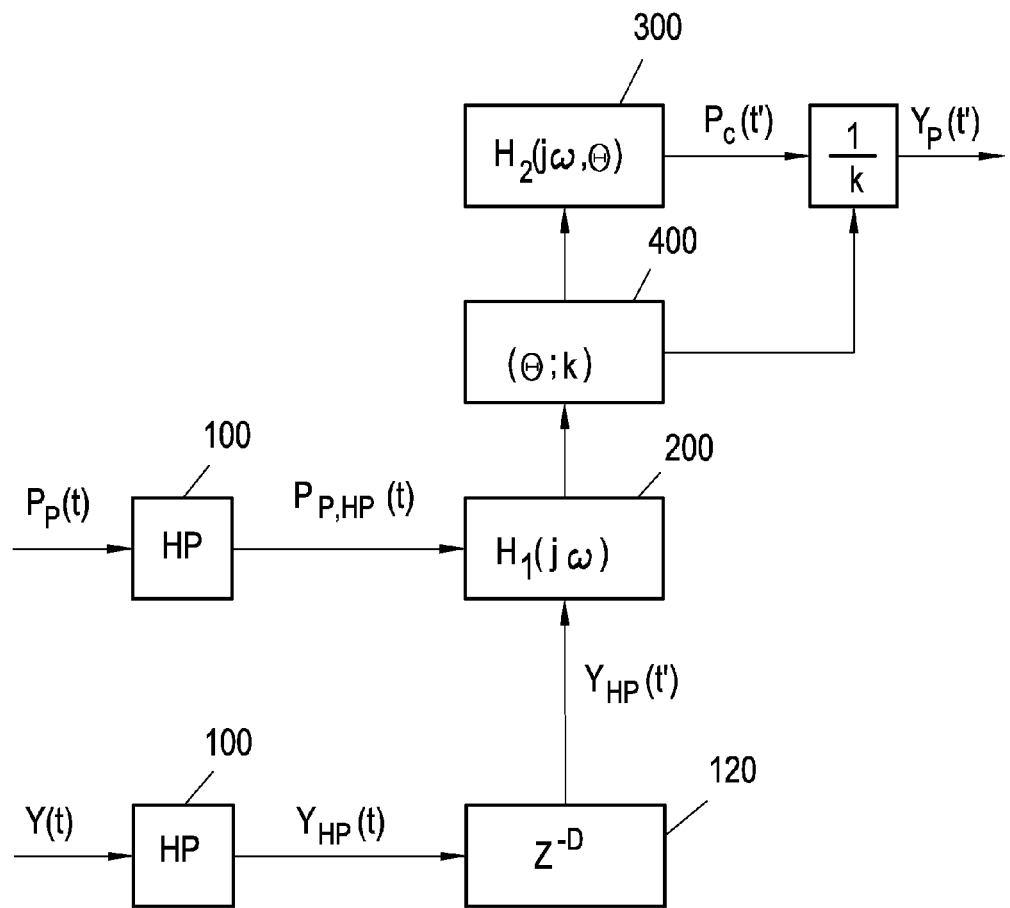
FIG. 5 is a drawing which illustrates a scheme for the determination of the arterial blood pressure $P_C(t)$ using a transmission algorithm.

FIG. 5 shows in a schematic illustration a simplified concept scheme for the determination of the arterial blood pressure $P_C(t)$ using a transmission algorithm.

The bioimpedance measuring device of the device according to the invention captures admittance measurement signals $Y(t)$, which are subsequently filtered by means of a high-pass filter 100 so that the lower-frequent signal components are separated and there are received signals of a filtered admittance $Y_{HP}(t)$. As the measured peripheral pressure signal $P_P(t)$ follows the respective central arterial pressure signal $P_C(t)$ to be determined, it is necessary to delay the transfer of the measured admittance signal $Y(t)$ or the corresponding signal of the filtered admittance $Y_{HP}p(t)$ in time and, in this way, provide for a correlation in time of the transmission algorithm. For this reason, there is provided a delay line 120, which transfers the filtered admittance signal $Y_{HP}(t')$ delayed in reference to the admittance signal $Y_{HP}(t)$ to the adaptive filter 200. The point of time t' is thus slightly delayed in reference to the point of time t.

The pressure signals $P_P(t)$ captured by the device for blood pressure measurement of the device are then also filtered by means of a high-pass filter 100, whereupon there is received a filtered pressure signal $P_{P,HP}(t)$. An adaptive filter 200 is used in order to determine a transmission function $H_1(j\omega)$ from the filtered pressure signal $P_{P,HP}(t)$ to the filtered admittance $Y_{HP}(j\omega)$.

There is further used a transmission algorithm 300 in order to determine an extrapolated transmission function $H_2(j\omega,\theta)$. For this reason, there is used an optimization algorithm 400 in order to, for example, according to the method of the least error squares, determine a parameter vector θ of the used transmission algorithm 300 as well as the scaling factor k so that the error between the filtered transmission function $H_1(j\omega)$ and the product of the scaling factor k is minimized with the extrapolated transmission function $H_2(j\omega,\theta)$ in a higher-frequent measurement range.

The arterial blood pressure $P_C(t)$ is determined using the extrapolated transmission function $H_2(j\omega,\theta)$ and the pressure signal $P_P(t)$. The pulse admittance $Y_P(t)$ for the reconstruction of the share of the respiration admittance $Y_B(t)$ is received using the product of the scaling factor k with the extrapolated transmission function $H_2(j\omega,\theta)$ and the pressure signals $P_P(t)$.

Figure 6:
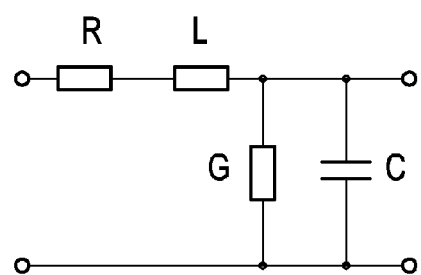
FIG. 6 is a drawing which illustrates the substitution circuitry of the transmission line model as transmission algorithm.

FIG. 6 shows schematically the substitution circuitry of the transmission line model as transmission algorithm. The parameter vector (θ) of the model comprises a flow resistance parameter (R), a resistance parameter (L) of the blood mass against acceleration, an elasticity parameter (C) as well as a porosity parameter (G).

The invention claimed is:

1. A determination device for the non-invasive determination of arterial blood pressure of a human or animal body, comprising:
at least a bioimpedance measuring device having a plurality of electrode pairs for capturing the admittance signals (Y(t)) caused by an impressed alternating current which electrode pairs are configured to be arranged at a distance from each other on at least one first section of the body, wherein the captured admittance signals (Y(t)) correspond to a composite signal made of signal components of a pulse admittance ($Y_P(t)$), a respiration admittance ($Y_B(t)$), a base admittance ($Y_0(t)$); and at least one blood pressure measurement device for the non-invasive measurement of the blood pressure; and
a processor of the determination device, which processor separates from the admittance measurement signals (Y(t)), which are received by the bioimpedance measuring device from several electrode pairs which electrode pairs are configured to be arranged at a distance from each other on at least one first section of the body, wherein the measurements are carried out multiple times, each time using electrode pairs arranged at different sites of the body and/or at respectively different measuring frequencies, at least the signal components of the pulse admittance ($Y_P(t)$) and which determines the arterial blood pressure ($P_C(t)$) from pressure signals ($P_P(t)$) of a second section of the body, which second body section is preferably disposed at a distance from the first body section, which pressure signals are received from the blood pressure measuring device for determining a scaling factor (k),
wherein the processor of the determination device determines the arterial blood pressure ($P_C(t)$) according to the following scheme:
measuring of several admittance measurement signals ($Y_1(t), Y_2(t)$) received by the bioimpedance measuring device from several electrode pairs which electrode pairs are configured to be arranged at different body sites and/or at different measuring frequencies;
filtering the admittance measurement signals (($Y_1(t), Y_2(t)$)) with a high-pass filter so that lower-frequency components of the base admittance ($Y_{1,0}(t), Y_{2,0}(t)$) are separated and filtered admittance signals ($Y_{1,HP}(t), Y_{2,HP}(t)$) are received;
setting sum equations, taking into account proportional factors ($k_{1,1}, k_{1,2}, k_{2,1}, k_{2,2}$) of the pulse admittance ($Y_P(t)$) as well as the respiration admittance ($Y_B(t)$) for the filtered admittance signals:

$Y_{1,HP}(t) = k_{1,1} \cdot Y_B(t) + k_{1,2} \cdot Y_P(t)$ $Y_{2,HP}(t) = k_{2,1} \cdot Y_B(t) + k_{2,2} \cdot Y_P(t);$ using a source separation algorithm in order to determine the proportional factors as well as the source signal components of the pulse admittance ($Y_P(t)$) and the respiration admittance ($Y_B(t)$) from the sum equations;
measuring pressure signals ($P_{1,P}(t), P_{2,P}(t)$) as reference pressure signals;
determining a scaling factor (k) and an offset value (d) so that the pulse admittance ($Y_P(t)$) coincides with the pressure signals ($P_{1,P}(t), P_{2,P}(t)$) measured as reference pressure signals:

$P_{1,P}(t) = k \cdot Y_{P,Sys} + d$ $P_{2,P}(t) = k \cdot Y_{P,Dia} + d;$ and after the end of the reference measurement, the arterial blood pressure ($P_C(t)$) is determined using the scaling factor (k) and the offset value (d) according to $P_C(t) = k \cdot Y_P(t) + d$.

2. The device according to claim 1 wherein the blood-pressure measurement device triggers the non-invasive blood pressure measurement discontinuously.

3. The device according to claim 1 wherein the blood-pressure measurement device triggers the non-invasive blood pressure measurement continuously.

* * * * *